United States Patent [19]

Nose et al.

[11] Patent Number: 4,901,582
[45] Date of Patent: Feb. 20, 1990

[54] FIXTURE FOR BRITTLE PRE-CRACK INTRODUCTION IN CERAMIC SPECIMEN

[75] Inventors: Tetsuro Nose; Toshimitsu Fujii, both of Kanagawaken, Japan

[73] Assignee: Nippon Steel Corporation, Tokyo, Japan

[21] Appl. No.: 139,259

[22] Filed: Dec. 29, 1987

[30] Foreign Application Priority Data

Dec. 29, 1986 [JP] Japan ............................. 61-315639

[51] Int. Cl.$^4$ ............................................. G01N 19/08
[52] U.S. Cl. ......................................... 73/799; 73/851
[58] Field of Search ................. 73/844, 845, 799, 12, 73/788, 856, 860, 851, 849, 852

[56] References Cited

U.S. PATENT DOCUMENTS 3,285,060 11/1966 Pessen .................................. 73/844

FOREIGN PATENT DOCUMENTS 0063237 5/1981 Japan ................................... 73/788
0089538 5/1986 Japan ................................... 73/799
0911244 3/1982 U.S.S.R. .............................. 73/788

OTHER PUBLICATIONS

Sadahiro, Takeshi, Transverse Rupture Strength and Fracture Toughness of WC—Co Alloys, 1981, pp. 291-295.
Nose, Tetsuro and Fujii, Toshimitsu, Evaluation of Fracture Toughness for Ceramic Materials by a Single—Edged—Precracked—Beam Method, 1988, pp. 328-333.

Primary Examiner—Jerry W. Myracle
Attorney, Agent, or Firm—Wenderoth, Lind & Ponack

[57] ABSTRACT

A fixture capable of a brittle pre-crack introduction of prescribed shape and size in a ceramic specimen with high reproducibility comprises an anvil provided on the upper side thereof with a central groove perpendicularly intersecting a specimen to be mounted thereon for pre-crack introduction and a groove for positioning the specimen and a platelike pusher possessing a smooth and flat lower surface. To ensure stability of the brittle pre-crack introduction, the positioning groove in the anvil is so formed as to rise rectangularly in an equal length on either side of the central groove and the overall length of the positioning groove, i.e. the sum of the lengths of the raised portions plus the width of the central groove, is kept from exceeding the length of the specimen. To enhance the results of the introduction, the lower surface of the pusher is finished with roughness of not more than 0.8S and flatness of not more than 0.01 mm.

18 Claims, 8 Drawing Sheets

Lower surface roughness not more than 0.8S
Flatness 0.01

Fig. 4 (b)

Ceramics

Fig. 4 (c)

Metal
Ceramics plate
Joint surface — Roughness not more than 0.8S
Flatness not more than 0.01mm

FIXTURE FOR BRITTLE PRE-CRACK INTRODUCTION IN CERAMIC SPECIMEN

BACKGROUND OF THE INVENTION

1. FIELD OF THE INVENTION

This invention relates to a fixture for introducing in a single edge of a beam-shaped specimen of a rigid brittle material such as ceramic material a prescribed pre-crack necessary for the test to be performed in evaluation of fracture toughness of the material.

2. DESCRIPTION OF THE PRIOR ART

Preparatory to design and use of a structure or a structural part, the various properties of the material used therefor must be precisely comprehended. The value of fracture toughness proves to be the most important of all of the characteristic values and is determined in the test for fracture toughness. For metallic materials which have demonstrated their attributes through long use, the method for introducing a fatigue pre-crack in a specimen prepared for the test of fracture toughness has been prescribed in ASTM E399 A2 for the purpose of pemitting acquisition of the value of fracture toughness appropriate from the viewpoint of fracture mechanics. To be specific, a pre-crack fulfilling such a necessary condition that the radius of curvature at the crack front should be such as to be regarded as substantially infinitesimal must be introduced by causing growth of a fatigue crack under the restricted condition that the stress intensity factor, $K_I$ should be not more than 60% of the fracture toughness, $K_{IC}$ of the material under test.

In such rigid and brittle materials as bearing steel, hard tool alloys, and ceramics, however, it is difficult to effect the controlled introduction of a prescribed fatigue pre-crack because the extension of a fatigue crack occurs at a notably high speed or, conversely, it takes an extremely long time before the pre-crack extends to a prescribed length because the extension of the fatigue crack proceeds very slowly. In any event, the introduction of a fatigue pre-crack in a rigid brittle material has proved to lack practicability in industrial use.

Figure 1A:
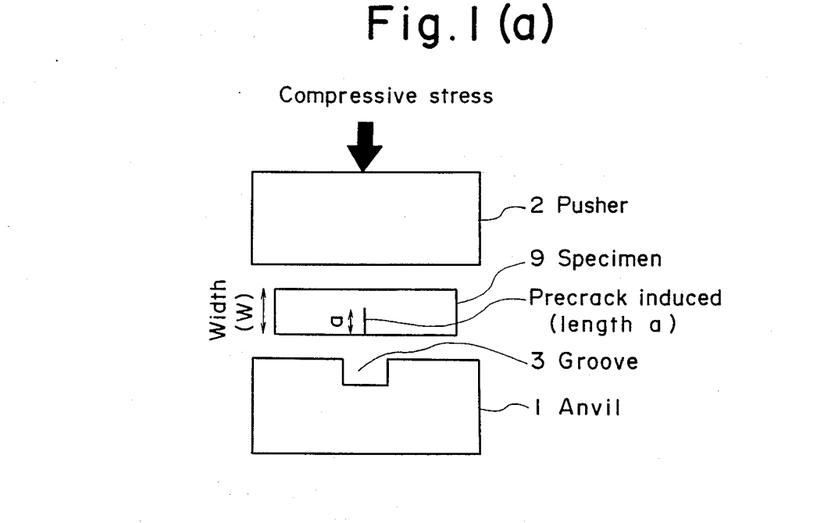
Figure 1B:
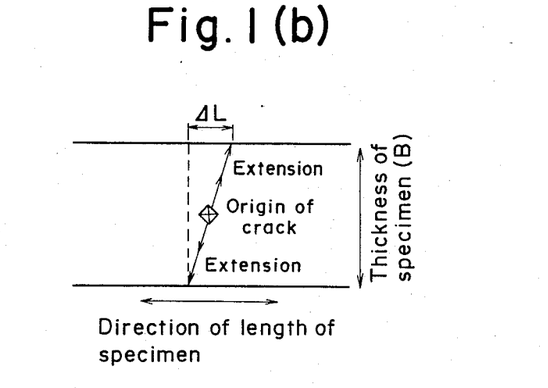
Figure 1C:
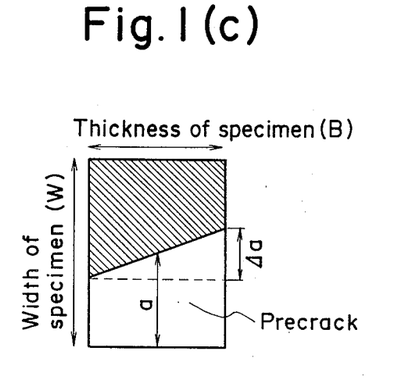
Figure 1D:
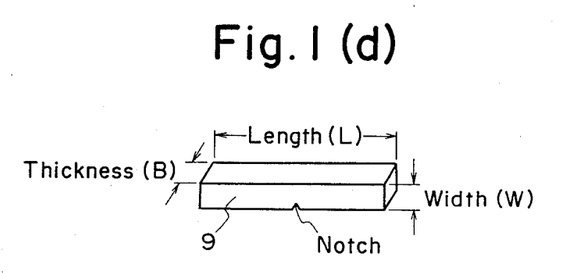

To solve the difficulty, a method has been recently devised and put to use which introduces a brittle pre-crack in a specimen from such materials as used for bearing steel and hard tool alloys, for example (Literature 1-S. Nunomura and S. Jitsukawa; Tetsu-to-Hagane, 64(1978), S853, Literature 2-T. Sadahiro; Journal of Japan Institute of Metals, 45(1981), p. 291, and Literature 3-R. Warren and B. Johannesson, Powder Metallurgy, 27(1984) p. 25). This method comprises mounting on an anvil possessing a groove at the center a beam-shaped specimen having an impression or a shallow notch formed in advance therein as illustrated in FIG. 1(d) such that the specimen perpendicularly intersects the groove as illustrated in FIG. 1(a), superposing on this specimen a pusher-possessing a flat lower surface, applying a compressive load on the specimen in the direction of the width (W) of the specimen thereby causing the free surface of the specimen above the groove of the anvil to protrude slightly into the groove and, by virtue of the protrusion, causing the surface portion of the aforementioned free surface of the specimen to generate tensile stress and induce a brittle crack extending from the aforementioned impression or notch. By this method, introduction of a brittle pre-crack of a prescribed length "a" is attained because the extension of the crack in the direction of the width (W) of the specimen ceases as the tensile stress rapidly dwindles with the growth of the crack. The brittle pre-crack which is introduced by this method has an extremely sharp front. In this respect, this method produces a pre-crack appropriate from the viewpoint of fracture mechanics. The method for the introduction of a brittle pre-crack described above is excellent in the sense that the introduction of the pre-crack is attained very quickly and conveniently as compared with the introduction of a fatigue pre-crack.

As concerns the calculation of the fracture toughness, $K_{IC}$ this value $K_{IC}$ is obtained by using actual test data in the computation of a mathematical formula which is derived from numerical analysis based on fracture mechanics. This analysis entails an indispensable precondition that the actually introduced pre-crack should substantially equal the hypothetical pre-crack in size and shape. For this reason, ASTM E399, besides the aforementioned provisions of A2 setting forth the conditions of stress in the introduction of fatigue pre-crack, covers provisions on the critical values such as of the inclination of extension of pre-crack and the deflection of course of extension, for example, in Paragraph 8.2 concerning the size and shape of the introduced fatigue pre-crack. Specifically, it is specified that the difference, $\Delta a$, of pre-crack length between the two lateral surfaces illustrated in FIG. 1(c) should be within 10% of the average value, a, of the pre-crack length on the fractured surface of the specimen and that the deflection of the plane direction of the extension of the pre-crack illustrated in FIG. 1(c) should be within 10° from the plane orthogonal to the direction of the length of the specimen. (The former value will be referred to hereinafter as the inclination, $\Delta a/a$, of the extension of the crack and the latter value as the deflection, $\Delta L/B$, of the course of extension. The conditions, $\Delta a/a \leq 0.10$ and $\Delta L/B \leq \tan 10° = 0.176$, are indicated in ASTM E399, paragraph 8.2.)

The method for the introduction of a brittle precrack described above accords with the provisions of ASTM E399 in the sense that the radius of curvature of the pre-crack front can be regarded as a substantial infinitesimal amount. Since the extension and the cessation of the brittle crack both occur instantaneously, however, it is difficult to control the inclination of the extension of pre-crack and the deflection of course of extension while the growth of the pre-crack is in progress. This method, therefore, has a disadvantage in that it does not always fulfil the aforementioned provisions easily. Particularly in the case of ceramics, since the blank materials and the finished products are mostly in small sizes, the test is inevitably required to be performed on specimens of small dimensions. Moreover, the ceramics by nature possess very low toughness. The size and shape of the brittle pre-cracks to be introduced by this method, therefore, are conspicuously affected by numerous delicate factors such as, for example, deflection of the specimen from the position perpendicularly intersecting the central groove in the anvil, dispersion in the length in which the anvil supports the specimen, roughness and flatness of the lower surface of the pusher, rigidity of the pushher and the anvil, and deflection of mutual disposition of the pusher, the specimen, and the anvil.

SUMMARY OF THE INVENTION

An object of the present invention, therefore, is to provide a fixture which, in the brittle pre-crack introduction in a beam-shaped specimen of a ceramic material, permits the pre-crack of a prescribed shape to be introduced with high reproducibility.

The other objects of this invention will become more apparent from the description given hereinbelow with reference to the accompanying drawings.

BRIEF DESCRIPTION OF THE DRAWINGS

FIGS. 1(a)–(d) are diagrams depicting a basic concept of the brittle pre-crack introduction in a beam-shaped specimen for the test of fracture toughness; FIG. 1(a) shows a cross section illustrating the principle of the pre-crack introduction, FIG. 1(b) a plan view illustrating a deflection of the course of extension of crack on the surface of the specimen, FIG. 1(c) a model diagram illustrating an inclination of the extension of crack on the fractured surface of the specimen, and FIG. 1(d) a perspective view of the beam-shaped specimen.

FIGS. 5(a)–(b) depict a typical fixture of this invention which uses a pusher provided with an outer frame.

FIGS. 6(a)–(b) show a diagram depicting an application of the fixture of this invention to a specimen of a shape other than is prescribed herein.

DETAILED DESCRIPTION OF THE INVENTION

This invention specifically is directed to preferred a fixture for the brittle pre-crack introduction in a ceramic specimen, which comprises an anvil provided on the upper side thereof with a central groove perpendicularly intersecting a specimen and a groove perpendicularly intersecting a specimen and a groove for positioning the specimen and a platelike pusher possessing a smooth flat lower surface. The positioning groove is so formed as to rise orthogonally in an equal length on either side of the central groove and the preferred overall length of this positioning groove, i.e. the sum of the lengths of the raised portions plus the width of the central groove, is not more than the length of the specimen. The lower surface of the pusher possesses roughness of not more than 0.8S specified in JIS B0601 and flatness of not more than 0.01 mm specified in JIS B0621. Further, at least the lower side of the pusher is made of a ceramic material. Otherwise, the pusher is a product obtained by preparing a metallic pusher having the lower surface thereof finished with roughness of not more than 0.8S and flatness of not more than 0.01 mm, preparing a ceramic plate having the surface thereof for contact with the metallic pusher finished with roughness of not more than 0.8S and flatness of not more than 0.01 mm, and joining the metallic pusher and the ceramic plate by the finished surfaces thereof. The pusher is provided with an outer frame fitting the outer surface of the anvil.

Figure 2:
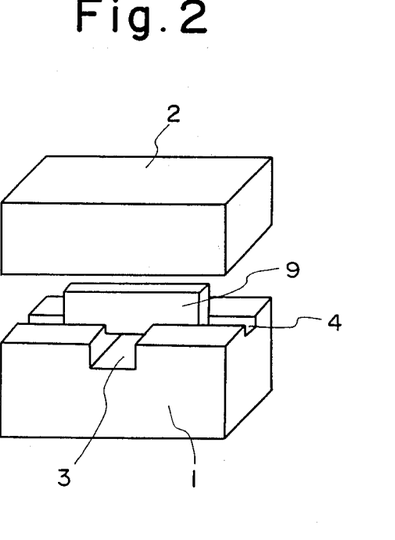
FIG. 2 is a perspective view illustrating a typical fixture as one embodiment of this invention.

FIG. 2 depicts a typical fixture of this invention to be used in the brittle pre-crack introduction in a beam-shaped specimen of a ceramic material. In FIG. 2, 1 denotes an anvil, which is provided at the center in the upper surface thereof with a groove 3 adapted to intersect a specimen orthogonally.

By 4 is denoted a positioning groove which is disposed perpdendicularly to the central groove 3 in a depth smaller than the central groove in a width substantially equal to the thickness of a specimen. A pusher 2 is in the shape of a plate possessing a smooth and flat lower surface, the pusher being movable in a direction perpendicular to the bottom surface of the positioning groove 4. A beam-shaped specimen 9 has a notch or an impression formed in advance at the center in one of the opposite surfaces orthogonal to the width of the specimen, namely in the lower surface thereof. As the material for the anvil 1 and the pusher 2, a steel material proves to be suitable in terms of ease of fabrication. Ceramics and other similarly rigid materials which are capable of withstanding the load necessary for the crack introduction are other possible materials.

Figure 3A:
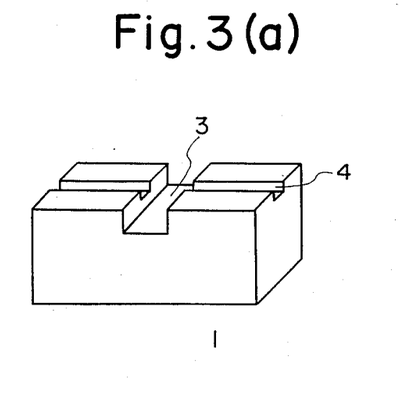
FIGS. 3(a), (b), (c), and (d) are perspective views illustrating typical anvils usable for the fixture of the present invention
Figure 3B:
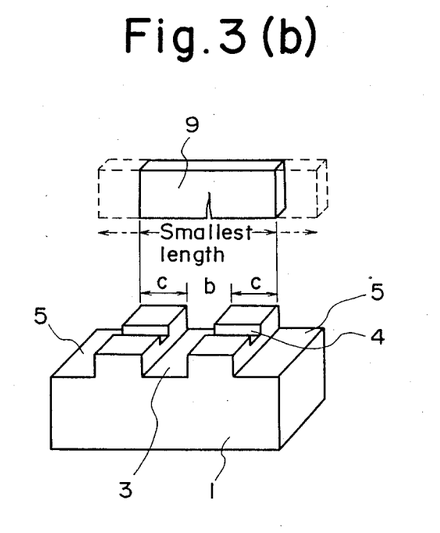
Figure 3C:
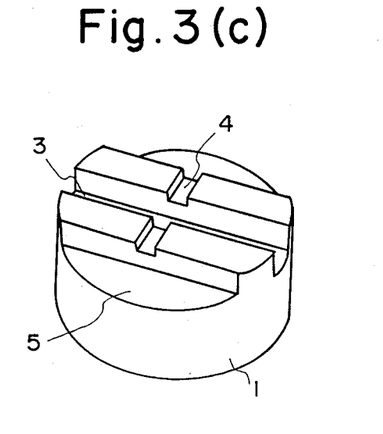
Figure 3D:
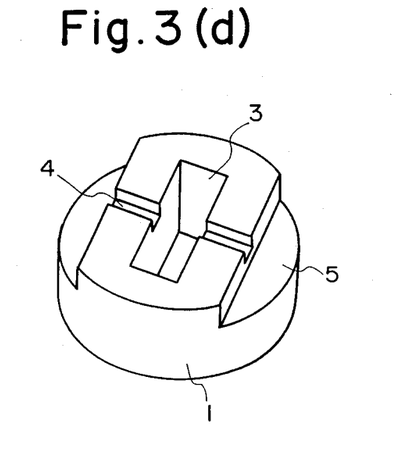

The visible shapes of the anvil and the pusher are not limited to those rectangular shapes illustrated in FIG. 2 but may be circular or elliptical shapes as illustrated in FIG. 3(c) and (d), for example.

The dimensions of the anvil and the pusher are to be selected in accordance with the size of a specimen which is subjected to the crack introduction. Frequently, the fixture is relatively small because ceramic specimens are generally small. In the case of a specimen measuring 3 mm in thickness, 4 mm in width, and 18 to 40 mm in length, for example, an anvil shaped as illustrated in FIG. 2 is formed in a length of 46 mm so that the anvil is longer than the specimen, a width of 30 mm, and a height of 10 t 15 mm and a pusher is formed in substantially equal dimensions, i.e. a length of 46 mm, a width of 30 mm, and a height of 10 to 15 mm. They are made of a steel material specified in Japanese Industrial Standard (JIS) G4051 S45C. The central groove 3, as described fully later on, is intended to permit protrusion of the specimen. The width (b) of this groove is fixed in accordance with the finite length (a) of a crack to be introduced in the specimen. This groove must be formed symmetrically relative to the center line of the anvil. The groove 3 may be formed so as to extend throughout the entire width of the anvil as illustrated in FIG. 2. Otherwise, it can be formed only in the indispensable portions to be perpendicularly intersected by the specimen as illustrated in FIG. 3(d). The depth of the groove 3 need not be particularly limited but may be decided in due respect of the shape, strength, etc. of the anvil.

The positioning groove 4 is disposed perpendicularly to the central groove 3 in a depth smaller than the depth of the central groove 3 and in a width substantially equal to the thickness (B) of the specimen 9. In order for the specimen to intersect the central groove exactly perpendicularly, the difference between the thickness (B) of the specimen and the width of the groove 4 is desired to be not more than 0.5 mm. The depth of the positioning groove 4 must be fixed in consideration of the size, material, etc. of the specimen so that when the specimen is disposed along the groove and the pusher is superposed on the specimen, the specimen is immobilized and the difference of height between the bottom surface of the positioning groove 4 and the bottom surface of the central groove 3 is sufficient for the specimen 9 to cause protrusion of the lower surface thereof. The length of the positioning groove 4 must be fixed in accordance with the length of the specimen subjected to the test.

The bottom surface of the positioning groove 4 must be finished smoothly and flatly so as to ensure exertion of a uniform load to the specimen. To be more specific, the finished bottom surface is desired to possess roughness of not more than 0.8S in terms of the maximum height specified in Japanese Industrial Standard (JIS) B0601 and flatness of not more than 0.01 mm in terms of the magnitude specified in JIS B0621. The values of roughness and flatness to be mentioned hereinafter in this specification are those determined in accordance with the relevant provisions of JIS B0601 and JIS B0621 respectively.

To be used for specimens (measuring 3 mm in thickness, 4 mm in width, and 18 to 40 mm in length), a typical anvil of the construction described above may be formed in a length of 40 to 50 mm, a width of 30 mm, and a height of 10 to 15 mm, as provided with a central groove 3 possessing a width (b) of 3 to 6 mm, a length of 30 mm, and a depth of 2 mm and a perpendicularly intersecting groove 4 possessing a width of 3.2 mm, a length of 18 to 50 mm, and a depth of 1 mm.

Preparatory to the brittle pre-crack introduction in the specimen 9 as illustrated in FIG. 2, the beam-shaped specimen as illustrated in FIG. 1(d) is disposed along the positioning groove 4 of the anvil 1 in such a manner that the lower surface of the specimen containing the impression or notch falls on the lower side and the aforementioned impression or notch falls approximately at the center of the central groove 3. Then, the pusher 2 is lowered into contact with the upper surface of the specimen 9 and a loading device (not shown) is actuated to exert a load on the pusher. By the compressive load transmitted to the specimen 9 through the pusher, the lower surface of the specimen above the central groove 3 of the anvil 1 is slightly protruded into the groove 3. By this protrusion, the specimen generates tensile stress in the lower surface thereof and induces a brittle crack extending from the notch or impression. As the crack extends in the direction of the width of the specimen 9, the tensile stress is alleviated so much as to stop the growth of crack. As the result, a brittle crack of a prescribed length is introduced in the specimen.

Since the anvil of the present invention is provided with the groove 4 for positioning the specimen, the specimen disposed in the groove 4 is automatically allowed to intersect the groove 3 exactly perpendicularly. Thus, the anvil of the present invention precludes the possibility of the course of extension of the brittle pre-crack deflecting in the direction of the length of the specimen as illustrated in FIG. 1(b) when the specimen is not disposed so as to intersect the central groove 3 exactly perpendicularly.

As demonstrated in Example 1, the fixture of the present invention permits a crack of only minimal deflection of the course of extension to be introduced in the specimen with high reproducibility.

The tensile stress which is generated in the lower surface of the specimen when the pusher exerts a compressive load on the specimen is variable with the width of the central groove 3. The length a of the brittle crack to be introduced in the specimen, therefore, is varied accordingly. Thus, the width of the central groove must be varied in accordance with the necessary length of the crack desired to be introduced. When the thickness of the specimen is varied, the width of the positioning groove must be accordingly varied.

Figure 3E:
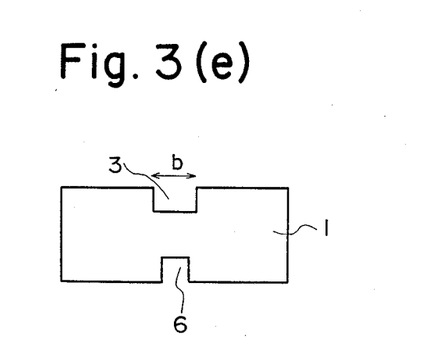
FIG. 3(e) is a cross section illustrating a typical anvil provided with a groove in the upper and lower surfaces thereof respectively.

When the anvil is provided on the lower side thereof with a groove 6 of a width different from the width of the groove on the upper side thereof as illustrated in FIG. 3(e), it has only to be turned upside down to change the width of the central groove as mentioned above. The necessity for preparing a multiplicity of anvils can be reduced by half by providing the anvil also on the lower side thereof with another combination of a central groove and a positioning groove. The central groove possesses different widths from their counterparts on the upper side. The anvil of this construction proves to be advantageous in terms of storage and operational efficiency.

Incidentally, the tensile stress generated in the free surface at the center of the specimen is varied with the width (b) of the central groove 3 as already described above. It is also affected by the lengths (c) of the specimen portion to be supported as illustrated in FIG. 3(b). When the terminal portions of the specimen are located inside of the positioning groove, the length (c) may vary specimen by specimen, resulting in the variation of the tensile stress. Therefore, the length of the pre-cracks introduced in these specimens may unexpectedly vary from specimen to specimen, even though the same anvil is used for the pre-crack introduction.

If the groove in the anvil is unduly long relative to the length of the specimen, there may ensure a disadvantage in that abnormal concentration of stress occurs in the terminal portions of the specimen in the direction of the length thereof to induce such adverse phenomena as breakage of the terminal portion, deflection of the course of extension of a crack, and inclination of the extension of crack when the anvil yields to plastic deformation.

This invention, therefore, contemplates in a preferred embodiment thereof forming the positioning groove 4 in the upper surface of the anvil to rise rectangularly in an equal length (c) on either side of the central groove 3 as illustrated in FIG. 3(b) and, further, preventing the overall length of the positioning groove, i.e. the sum of the lengths of the raised portions (2c) plus the width (b) of the central groove 3, (2c+b) from exceeding the length of the specimen.

In a preferred embodiment, the extreme portions of the positioning groove 4 in the upper surface of the anvil which remain outside the portions raised perpendicularly in an equal length on either side of the central groove 3 are cut to a depth greater than at least the depth of the positioning groove 4 in the raised so as to form corner groove 5. The corner grooves may be formed toward the outer edges of the anvil parallel to the central groove 3 as illustrated in FIG. 3(b), whereas the embodiment shown in FIG. 3(a) does not have such corner grooves. Otherwise, they may be formed only in the extended portions of the groove 4. In this construction of the positioning groove, the specimen supporting lengths (c) are fixed without reference to the length of the specimen and, as the result, the pre-crack length in the specimen is likewise fixed.

Since the extreme portions of the specimen in the direction of length protrude from the supporting portions of the anvil, no concentration of stress can occur in the extreme portions of the specimen. As the result, the deflection of the course of crack extension and the inclination of the extension of pre-crack can be precluded.

The pusher 2 is intended to contact the surface of the specimen corresponding to the thickness thereof and transmit the load to the specimen from a loading device (not shown). For the purpose of preventing the pusher 2 from exerting an unevenly distributed load on the specimen and consequently inducing an alteration in the shape of the crack, the pusher 2 requires the lower surface thereof to be finished smoothly and flatly.

For effective reception of the load from the loading device, the pushehr 2 is desired to be provided thereon with a spherical mechanism. To permit effective direct contact with the pressure board, the pusher is desired to be formed in the shape of a board.

As the material for the pusher, an iron or steel material proves to be suitable in terms of ease of fabrication. Ceramics and other similarly rigid materials which are capable of withstanding the load necessary for the introduction of a crack are also possible materials.

Figure 4A:
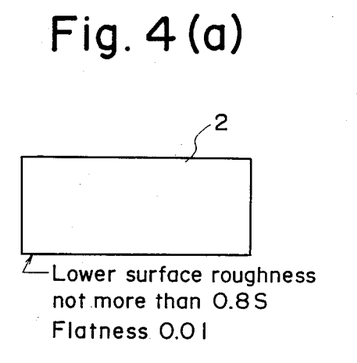
FIGS. 4(a)–(c) show cross sections illustrating a typical pusher to be used in the fixture of this invention.

The uniformity and the symmetry of the load transmitted from the pusher to the specimen are essential conditions for ensuring high reproducibility of the pre-crack introduction of prescribed shape to specimens. Particularly, it is necessary to control optically the roughness and the flatness of the lower surface of the pusher 2 (particularly the portion of the surface used for the exertion of the load on the specimen) as illustrated in FIG. 4(a).

In the present invention, therefore, the lower surface of the pusher is desired to be finished with a roughness of not more than 0.8S and flatness of not more than 0.01 mm.

In accordance with the present invention, the deflection of the course of crack extension and the inclination of the extension of pre-crack can be controlled within the respectively prescribed ranges and, as the result, the pre-crack introduction of prescribed shape can be effected with high reproducibility.

As the material for the pusher, a metallic material is excellent in terms of ease of fabrication as described previously. The pusher made of such a metallic material, however, is susceptible of plastic deformation during the transmission of load to the specimen. Even when this pusher has the lower surface finished to the prescribed roughness and flatness, the portion of the lower surface thereof which is exposed to contact with the edge portions of the specimen is liable to sustain a rugged dent or depression due to concentration of stress when the pusher is used time and again. The rugged dent thus formed interferes with desirable match of the specimen and the pusher and brings about such critical defects as breakage of the edge portion of the specimen, deflection of the course of crack extension, and inclination of the extension of pre-crack.

Figure 4B:
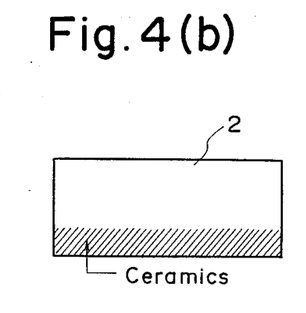

As a solution to this problem, the present invention contemplates forming at least the lower portion of the pusher with a ceramic material as illustrated in FIG. 4(b).

In this case, the pusher may be wholly formed with a ceramic material. The pusher with a lower ceramic surface is generally obtained by forming the pusher with a metallic material and joining a ceramic plate to the lower surface of the metallic pusher by cementation or adhesion. Otherwise, the ceramic layer may be formed by flame spraying or coating the lower surface of the metallic pusher with a ceramic substance.

As ceramics, zirconia, silicon nitride, and other similar materials can be used. The ceramic material thus employed is required to effect the transmission of the load with high uniformity and symmetry and warrant high durability to resist the impact of contact. The material for the ceramics and the strength of the produced ceramics are fixed in consideration of the various conditions discussed above.

When the lower portion of the pusher is formed with a ceramic material as demonstrated in Example 4 (Table 4, No. 10), the pusher enjoys warranted durability. As the result, the reproducibility of the pre-crack introduction of prescribed shape can be notably improved.

Figure 4C:
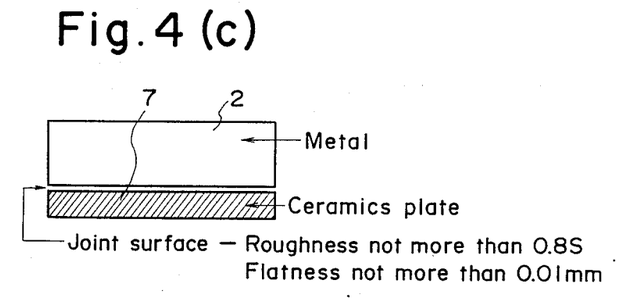

The effect of forming the power portion of the pusher 2 with a ceramic material is quite apparent as described above. When the pusher has at least the lower surface portion thereof formed with a ceramic material, such as when the pusher is provided thereon with a spherical mechanism as a means for enhancing the smoothness of the transmission of load from the loading device to the pusher, it is more efficient in the light of ease of fabrication to form with a metallic material the upper portion of the pusher intended for provision of the spherical mechanism and form with a ceramic plate the lower surface portion of the pusher intended for transmission of load to the specimen and subsequently joining the two portions fast. The union of the two portions in this case is attained most conveniently by adhesion with an adhesive agent. For the union, it is an essential condition that the joined portion should enjoy ample rigidity to realize highly uniform and symmetrical transmission of load to the specimen. The impartation of ample rigidity to the joined portion is attained by controlling the roughness and flatness of both the opposed surfaces of the joined portion, namely the lower surface of the pusher 2 made of metallic material and the upper surface of the ceramic plate 7 as illustrated in FIG. 4(c).

To be specific, the pusher in the present embodiment is a product obtained by preparing a metallic pusher having the lower surface thereof finished with roughness of not more than 0.8S and flatness of not more than 0.01 mm, forming a ceramic plate having the surface thereof for adhesion to the aforementioned lower surface finished with roughness of not more than 0.8S and flatness of not more than 0.01 mm, and joining the pusher and the plate by the two surfaces so finished.

The ceramic plate has only to possess a thickness enough for producing sufficient rigidity when it is joined to the metallic pusher. Generally, this thickness falls approximately in the range of 3 to 10 mm. As the adhesive agent for this union, an organic adhesive agent such as an epoxy type adhesive agent is used. The thickness of the ceramic plate, the kind of the adhesive agent, and the thickness of the adhesive agent must be selected so that the ceramic plate produces the necessary rigidity in conjunction with the metallic pusher.

The ceramic plate need not be attached to the entire lower surface of the metallic pusher but may be attached only to the portion of the lower surface destined to contact the specimen.

As clearly demonstrated in Example 5 (Table 5, No. 12), the deflection of the course of extension of the crack introduced in the specimen and the inclination of the extension of the crack can be decreased to a great extent by controlling the roughness and the flatness of the lower surface of the metallic pusher and the surface of the ceramic plate for adhesion to the aforementioned lower surface respectively below 0.8S and 0.01 mm.

Figure 5A:
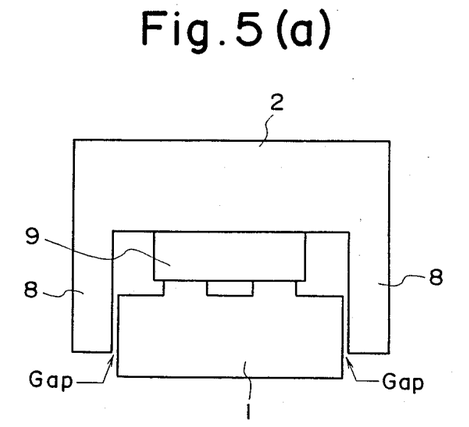
FIG. 5(a) shows a cross section and FIG. 5(b) shows a perspective view illustrating a modification having the frame fixed with a bolt.

To ensure a pre-crack introduction of prescribed size and shape, the anvil and the pusher must be designed and fabricated with meticulous care. It is equally important that the anvil, the specimen, and the pusher should be disposed with high exactitude. Such adverse phenomena as the deflection of the course of extension of crack and the inclination of extension of crack inevitably occur unless the anvil, the specimen 9, and the pusher 2 are so disposed that the center of the central groove 3 of the anvil, the center of the impression or notch in the lower surface of the specimen, and the center of the pusher fall substantially on one and the same vertical line. The present invention, therefore, contemplates providing the pusher 2 on the outer periphery thereof with an outer frame 8 fitting the outer surface of the anvil as illustrated in FIG. 5(a).

For the sake of the mutual positioning of the pusher and the anvil, the gap between the inner surface of the outer frame 8 and the outer surface of the anvil 1 is desired to be as small as permissible. To permit smooth insertion of the outer frame 8 around the anvil 1, however, this gap is required to be not less than 0.05 mm and not more than 0.5 mm and desired to be around 0.1 mm.

Figure 5B:
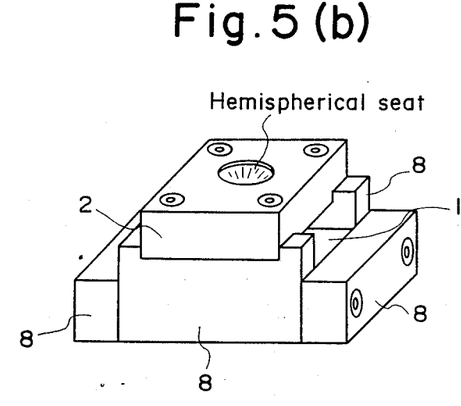

Though the outer frame 8 is desired to be formed with a metallic material or other material possessing similar rigidity, it may be molded integrally with the pusher 2. For the purpose of facilitating fine adjustment of this gap, the divisible segements of the pusher may be molded separately and assembled by being joined to the pusher proper with bolts, for example, as illustrated in FIG. 5(b).

As demonstrated in Example 6, the crack which is introduced in the specimen by the use of the pusher of this invention provided with the outer frame hardly suffers from the deflection of the extension course or the inclination of the extension. The introduction of crack enjoys high reproducibility.

Further, the outer surface of the outer frame 8 is convenient for attachment of a sensor which is adapted to detect an elastic wave or a sonic wave emitted during the growth of a brittle crack and display the occurrence of a crack in the specimen.

Figure 6A:
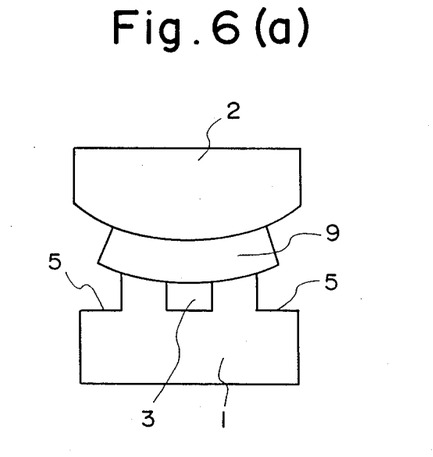
FIG. 6(a) shows a cross section illustrating a typical application to a specimen possessing a curved surface and FIG. 6(b) shows a perspective view illustrating a typical anvil to be used for a specimen in the shape of a deformed plate.
Figure 6B:
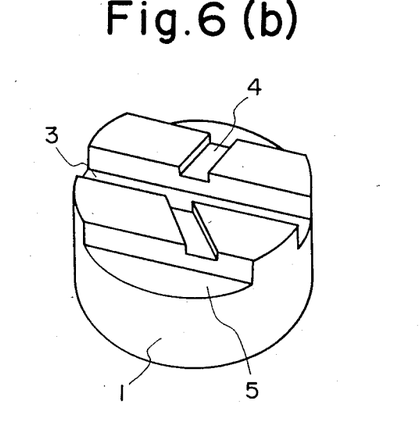

The use of the fixture of this invention need not be limited only to beam-shaped specimens. The fixture may be applied equally effectively to specimens of some other shape by suitably altering the shape of the positioning groove in the anvil and the shape of the lower surface of the pusher. For example, FIG. 6(a) depicts a case wherein the shape of the lower surface of the pusher and the shape of the positioning groove in the anvil are altered so as to adapt the fixture for use on specimens possessing a curved surface. FIG. 6(b) depicts a case wherein the shape of the positioning groove in the anvil is altered so as to adapt the fixture for use on specimens of a deformed shape. The utility of this invention can be expanded in scope by altering the shape of the anvil and that of the pusher in accordance with variable shape of a specimen.

EXAMPLE 1:

To produce a fixture of this invention, an anvil 30 mm in width, 14 mm in height, and 46 mm in length was formed with S45C. In the upper surface of this anvil, a central groove 5 mm in width, 30 mm in length, and 2 mm in depth was formed at the center and a positioning groove 3.2 mm in width, 46 mm in length (including the width of the central groove), and 1 mm in depth was formed perpendicularly to the central groove.

The bottom surface of the positioning groove was finished with roughness of not more than 0.8S and flatness of not more than 0.01 mm.

As a pusher, a plate 30 mm in width, 14 mm in height, and 46 mm in length was formed with S45C. The lower surface of this pusher was smoothly and flatly finished with roughness of not more than 0.8S and flatness of not more than 0.01 mm.

The specimen was a normal pressure sintered beam-shaped SiC piece 3.0 mm in thickness (B), 4.0 mm in width (W), and 18 mm in length (L). In the lower surface of the specimen, a notch was inserted through thickness direction at the center in the direction of length.

The specimen was set in place inside the groove 4 of the anvil and the pusher was mounted on the specimen. Then a loading device was actuated to exert a load on the pusher and introduce a brittle crack in the specimen. The specimen containing the crack was examined to determine the deflection, $\Delta L/B$ (mm/mm), of the course of extension of crack. Table 1 shows the results of Test No. 1 using the fixture of this invention and Test No. 2 using a fixture containing no groove in the anvil, each performed on three specimens.

TABLE 1

| No. | Positioning groove used | Deflection of course of extension, $\Delta L/B$ (mm/mm) | Remark |
| --- | --- | --- | --- |
| 1 | Yes | −0.01; 0.01; 0.01 | This invention |
| 2 | No | −0.31; 0.25; 0.32 | Conventional method |

(Material of specimens: Normal pressure sintered SiC pieces
Dimensions of specimens: 3 mm (B) × 4 mm (W) × 18 mm (L), 3 pieces)

It is clearly noted from the results that the fixture of the present invention permits a crack introduction of small deflection of course of extension with high reproducibility.

EXAMPLE 2:

A fixture of this invention was obtained by following the procedure of Example 1, excepting the positioning groove in the upper surface of the anvil was formed in two rectangularly raised portions of an equal length on either side of the central groove. Specifically, the positioning groove was formed by inserting spaced-apart cuts 14 mm in length and 2 mm in depth one at each of the extreme portions of the anvil parallel to the central groove. The raised portions of the positioning groove, therefore, had a length (supporting length (c)) of 6.5 mm on either side of the central groove and the overall length of the groove (2c+b) was 18 mm. The same SiC specimens as used in Example 1 were prepared in two lengths, 18 mm and 36 mm, and treated with the fixture produced as described above, for a crack introduction. The cracks thus introduced in the specimens were measured in length.

Test Nos. 3 and 4 used the fixture of the present invention and Test Nos. 5 and 6 used the conventional fixture the positioning groove of which was not of the type formed of raised portions, each performed on three specimens.

From the results it isnoted that the fixture of the present invention permits a crack introduction of a fixed length with high reproducibility without reference to the length of specimen.

TABLE 2

| No. | Anvil Width, b, of central groove | Width of cut | Supporting length, (c) | Length of specimen | Length of pre-crack (a), (mm) | Remark |
|---|---|---|---|---|---|---|
| 3 | | End portions | Opposite sides | 18 mm | 2.2; 2.4; 2.4 | This invention |
| 4 | 5 mm | 14 mm each | 6.5 mm each | 36 mm | 2.3; 2.4; 2.5 | |
| 5 | | 0 mm | 6.5 mm each | 18 mm | 2.2; 2.2; 2.4 | Conventional |
| 6 | | | 15.5 mm each | 36 mm | 1.3; 1.5; 1.6 | |

(Material of specimens: Normal pressure sintered SiC pieces
Dimensions of specimens: 3 mm (B) × 4 mm (W) × (L), 3 pieces)

EXAMPLE 3:

A fixture of this invention was obtained by following the procedure of Example 1, excepting the lower surface of the pusher was finished with roughness of 0.8S and flatness of 0.01 mm. With the fixture using this pusher, the same SiC specimens as used in example 1 were treated for a crack introduction. The cracks introduced in the specimens were examined as to deflection of course of extension of crack and inclination of the extension of crack. In Table 3, Test No. 7 used the fixture of this invention and Test Nos. 8 and 9 used conventional fixtures wherein the pushers had their lower surfaces finished with roughness of 1.6S and flatness of 0.01 mm and roughness of 0.8S and flatness of 0.02 mm respectively, each performed on three specimens. The data on the shape of crack introduced in the specimen are shown in the table.

TABLE 3

| No. | Roughness | Flatness (mm) | Frequency | Deflection, ΔL/B, of course of extension | Inclination, Δa/a, of extension of crack | Remark |
|---|---|---|---|---|---|---|
| 7 | 0.8S | 0.01 | 1 | −0.05; −0.02; 0.03 | −0.05; −0.02; 0.01 | This invention |
| 8 | 1.6S | 0.01 | 1 | −0.15; 0.11; 0.18 | −0.09; 0.21; 0.07 | Conventional |
| 9 | 0.8S | 0.02 | 1 | 0.14; 0.18; 0.21 | 0.08; 0.15; 0.12 | Conventional |

(Material of specimens: Normal pressure sintered SiC pieces
Dimensions of specimens: 3 mm (B) × 4 mm (W) × 18 mm (L), 3 pieces)

From the results, it is clearly noted that the deflection of the course of extension of crack and the inclination of the extension of crack could be controlled within the prescribed ranges and the introduction of a pre-crack of prescribed shape could be obtained with high reproducibility.

EXAMPLE 4:

A fixture of this invention was obtained by following the procedure of Example 1, excepting a Si$_3$N$_4$ plate 4.0 mm in thickness was attached fast with an epoxy type adhesive agent to the lower surface of the pusher.

With the fixture using this pusher, the same SiC specimens as used in Example 1 were treated for a crack introduction. The cracks introduced in the specimens were examined as to deflection of the course of extension of crack and inclination of the extension of crack.

In Table 4, Test No. 10 represents a case wherein the aforementioned fixture of this invention was repeatedly used for a crack introduction on 100 sets of the same SiC specimen as used in Example 1 and the 100th set of specimens was examined as to the shape of crack and Test No. 11 a case wherein a conventional fixture incorporating a pusher of medium carbon steel (S45C) and involving no adhesion of any ceramic piece was repeatedly used for a crack introduction on 10 sets of the same specimen and the 10th set of specimens was examined similarly. Each set comprises three pieces. It is noted from the results that when the fixture of this invention having a ceramic piece attached to the lower surface of a pusher was used, the crack in the 100th set of specimens involved only small deflection of the course of crack and small inclination of the extension of crack, indicating that this fixture was capable of introducing a crack of prescribed shape and size stably.

TABLE 4

| No. | Material of lower surface of pusher | Frequency | Deflection, ΔL/B, of course of extension | Inclination, Δa/a, of extension of crack | Remark |
|---|---|---|---|---|---|
| 10 | Sintered Si$_3$N$_4$ piece | 100 | −0.01; 0.01; 0.01 | −0.05; 0.02; 0.04 | This invention |
| 11 | Medium carbon steel (S45C) | 10 | 0.17; 0.21; 0.27 | 0.19; 0.17; 0.24 | Conventional |

(Material of specimens: Normal pressure sintered SiC pieces
Dimensions of specimens: 3 mm (B) × 4 mm (W) × 18 mm (L), 3 pieces)

It is noted from the results that the pusher using a ceramic piece in the lower surface thereof enjoyed warranted durability and permitted introduction of a pre-crack of prescribed shape with high reproducibility.

EXAMPLE 5:

A fixture of this invention was obtained by following the procedure of Example 1, excepting a metallic pusher having the lower surface (surface for adhesion) thereof finished with roughness of 0.8S and flatness of 0.01 mm was prepared, a Si$_3$N$_4$ plate having a thickness of 4 mm and the same area as that of the lower surface of the metallic pusher (30 mm × 46 mm) and having the surface thereof for adhesion to the lower surface of the metallic pusher was formed, and a Si$_3$N$_4$ plate was attached fast with an epoxy type adhesive agent to the lower surface of the metallic pusher. The thickness of the adhesive agent layer was 0.02 mm. With the fixture using this pusher, the same specimens as used in Example 1 were treated for a crack introduction. In Table 5, Test No. 12 used the fixture incorporating the pusher obtained as described above and Test Nos. 13 and 14 used a conventional fixture wherein the pushers were finished to different degrees of roughness and flatness.

TABLE 5

| No. | Roughness | Flatness | Frequency | Deflection, ΔL/B, of course of extension | Inclination, Δa/a, of extension of crack | Remark |
|---|---|---|---|---|---|---|
| 12 | 0.8S | 0.01 mm | 100 | −0.01; 0.01; 0.01 | −0.05; 0.02; 0.04 | This invention |
| 13 | 1.6S | 0.01 | 1 | 0.12; 0.19; | 0.17; 0.15; | Conven- |

TABLE 5-continued

| No. | Rough-ness | Flat-ness | Fre-quen-cy | Deflec-tion, $\Delta L/B$, of course of extension | Incli-nation, $\Delta a/a$, of extension of crack | Remark |
|---|---|---|---|---|---|---|
|  |  | mm |  | 0.25 | 0.27 | tional |
|  |  |  |  | 0.18; | 0.19; | Con- |
| 14 | 0.8S | 0.02 | 1 | 0.23; | 0.15; | ven- |
|  |  | mm |  | 0.30 | 0.25 | tional |

(Material of specimens: Normal pressure sintered SiC pieces
Dimensions of specimens: 3 mm (B) × 4 mm (W) × 18 mm (L), 3 pieces)

It is noted from the results that the deflection of the course of extension of the introduced crack and the inclination of the extension of crack could be decreased to extremely low levels by finishing the joining surfaces of the metal pusher and the ceramic plate with roughness of not more than 0.8S and flatness of not more than 0.01 mm.

EXAMPLE 6:

A fixture of this invention was obtained by following the procedure of Example 1, excepting the pusher had an outer frame attached thereto. The outer frame was produced by preparing 4 S45C plates 8 mm in thickness, 46 mm in length, and 28 mm in width, placing the plates in such a manner that the upper end of the outer frame would fall flush with the upper surface of the pusher, and fastening them to the pusher with bolts. The outer frame thus completed was adjusted in position with the bolts so that the inner surface of the outer frame of the pusher and the outer surface of the anvil would be separated with a gap of 0.1 mm.

With the fixture using this pusher, the same specimens as used in Example 1 were treated for a crack introduction. The cracks thus introduced in the specimens wre examined as to the shape of crack.

In Table 6, Test No. 15 used the pusher of this invention provided with the outer frame as described above and Test No. 16 used a conventional pusher provided with no outer frame.

TABLE 6

| No. | Outer frame used | Fre-quency | Deflection, $\Delta L/B$, of course of extension | Inclination, $\Delta a/a$, of extension of crack | Remark |
|---|---|---|---|---|---|
|  |  |  | −0.01; | −0.05; | This |
| 15 | Yes | 100 | 0.01; | 0.02; | in- |
|  |  |  | 0.01 | 0.04 | vention |
|  |  |  | −0.35; | 0.30; | Con- |
| 16 | No | 1 | 0.13; | −0.22; | ven- |
|  |  |  | 0.20 | 0.35 | tional |

(Material of specimens: Normal pressure sintered SiC pieces
Dimensions of specimens: 3 mm (B) × 4 mm (W) × 18 mm (L), 3 pieces)

It is noted from the results that the use of the outer frame on the pusher permitted a crack of small deflection of course of extension and small inclination of extension to be introduced with high reproducibility.

The fixture of the present invention permits a brittle crack of prescribed size and shape to be easily introduced in a ceramic specimen with high reproducibility. This invention can be utilized for the brittle crack introduction in not merely ceramic specimens but also in specimens of other rigid and brittle materials. The fixture can be applied as effectively to specimens of shapes other than the shape of beam as to the beam-shaped specimens when the shape of the anvil and that of the pusher are altered suitably.

While the present invention has been described with reference to the foregoing embodiments, many changes and modifications may be made thereto which fall within the scope of the appended claims.

While the present invention has been described by means of specific embodiments, it is to be understood that numerous changes and modifications may be made therein without departing from the spirit and scope of the invention as defined in the appended claims.

What is claimed is:

1. A fixture for introducing with high reproducibility a pre-crack in a ceramic specimen which pre-crack has a predetermined length as taken in a widthwise direction of the specimen that is less than the entire width of the specimen, said fixture comprising an anvil provided on the upper side thereof with a central groove and a positioning groove disposed relative to said central groove so as to position a specimen having a thickness corresponding to the width of the positioning groove over and perpendicular to the central groove when the specimen is seated on the anvil in the positioning groove, and a platelike pusher possessing a smooth and flat lower surface for pushing the specimen seated in the positioning groove downward toward said central groove.

2. The fixture according to claim 1, wherein said positioning groove for positioning the specimen has portions extending an equal length on either side of said central groove, said groove portions having a bottom surface at a level above the level of the bottom of said central groove, and the sum of the lengths of said groove portions plus the width of said central groove, is to be not more than the length of the specimen.

3. The fixture according to claim 1, wherein at least the lower side of said pusher is formed with a ceramic material.

4. The fixture according to claim 3, wherein said pusher is provided on the outer periphery thereof with an outer frame fitting the outer surface of said anvil.

5. The fixture according to claim 1, wherein said pusher is provided on the outer periphery thereof with an outer frame fitting the outer surface of said anvil.

6. The fixture according to claim 1, wherein said pusher is movable in a direction perpendicular to a plane containing a bottom surface of said positioning groove.

7. The fixture according to claim 1, wherein said anvil has a length parallel to a length of the specimen when the specimen is seated on the anvil in the positioning groove and the length of said anvil is to be greater than the length of the specimen.

8. The fixture according to claim 1, wherein a depth of said positioning groove between an upper surface of said anvil and a bottom surface of said positioning groove is less than a width of the specimen, the width of the specimen extending in a direction perpendicular to said bottom surface of said positioning groove when the specimen is seated on the anvil in the positioning groove.

9. The fixture according to clam 1, wherein said pusher has a width measured in a direction parallel to a width of said central groove, the width of said pusher being greater than the width of said central groove.

10. A fixture for introducing with high reproducibility a pre-crack in a ceramic specimen which pre-crack has a predetermined length as taken in a width-wise direction of the specimen that is less than the entire width of the specimen, said fixture comprising an anvil provided on the upper side thereof with a central groove and a positioning groove disposed relative to said central groove so as to position a specimen having a thickness corresponding to the width of the positioning groove over and perpendicular to the central groove when the specimen is seated on the anvil in the positioning groove, and a platelike pusher possessing a smooth and flat lower surface for pushing the specimen seated in the positioning groove downward toward said central groove, the lower surface of said pusher having roughness of not more than 0.8S specified in JIS B0601 and flatness of not more than 0.01 mm specified in JIS B0621.

11. The fixture according to claim 10, wherein at least the lower side of said pusher is formed with a ceramic material.

12. The fixture according to claim 11, wherein said pusher comprises a metallic pusher having a lower finished surface thereof with roughness of not more than 0.8S specified in JIS B0601 and flatness of not more than 0.01 mm specified in JIS B0621, and a ceramic plate having an upper finished surface thereof in contact with said metallic pusher with roughness of not more than 0.8S specified in JIS B0601 and flatness of not more than 0.01 mm specified in JIS B0621, said metallic pusher and said ceramic plate having the finished surfaces thereof joined together.

13. The fixture according to claim 11, wherein said pusher is provided on the outer periphery thereof with an outer frame fitting the outer surface of said anvil.

14. The fixture according to claim 10, wherein said pusher is provided on the outer periphery thereof with an outer frame fitting the outer surface of said anvil.

15. A fixture for introducing with high reproducibility a pre-crack in a ceramic specimen which pre-crack has a predetermined length as taken in a width-wise direction of the specimen that is less than the entire width of the specimen, said fixture comprising an anvil provided on the upper side thereof with a central groove and a positioning groove disposed relative to said central groove so as to position a specimen having a thickness corresponding to the width of the positioning groove over and perpendicular to the central groove when the specimen is seated on the anvil in the positioning groove, and a platelike pusher possessing a smooth and flat lower surface for pushing the specimen seated in the positioning groove downward toward said central groove, at least the lower side of said pusher comprising a ceramic material, said pusher comprising a metallic pusher having a lower finished surface thereof with roughness of not more than 0.8S specified in JIS B0601 and flatness of not more than 0.01 mm specified in JIS B0621, and a ceramic plate having an upper finished surface thereof in contact with said metallic pusher with roughness of not more than 0.8S specified in JIS B0601 and flatness of not more than 0.01 mm specified in JIS B0621, said metallic pusher and said ceramic plate having the finished surfaces thereof joined together.

16. A fixture for introducing with high reproducibility a pre-crack in a ceramic specimen which pre-crack has a predetermined length as taken in a width-wise direction of the specimen that is less than the entire width of the specimen, said fixture comprising an anvil provided on the upper side thereof with a central groove and a positioning groove disposed relative to said central groove so as to position a specimen having a thickness corresponding to the width of the positioning groove over and perpendicular to the central groove when the specimen is seated on the anvil in the positioning groove, and a platelike pusher possessing a smooth and flat lower surface for pushing the specimen seated in the positioning groove downward toward said central groove, said positioning groove for positioning the specimen in said anvil having portions extending an equal length on either side of said central groove, said groove portions having a bottom surface at a level above the level of a bottom of said central groove, and the sum of the lengths of said groove portions plus the width of said central groove to be no more than the length of the specimen, at least the lower side of said pusher comprising a ceramic material.

17. The fixture according to claim 16, wherein said pusher comprises a metallic pusher having a lower finished surface thereof with roughness of not more than 0.8S specified in JIS B0601 and flatness of not more than 0.01 mm specified in JIS B0621, and a ceramic plate having an upper finished surface thereof in contact with said metallic pusher with roughness of not more than 0.8S specified in JIS B0601 and flatness of not more than 0.01 mm specified in JIS B0621, said metallic pusher and said ceramic plate having the finished surfaces thereof joined together.

18. The fixture according to claim 16, wherein said pusher is provided on the outer periphery thereof with an outer frame fitting the outer surface of said anvil.

* * * * *